(12) United States Patent
Tsujimoto (10) Patent No.: US 10,007,835 B2
(45) Date of Patent: Jun. 26, 2018

(54) CELL REGION DISPLAY CONTROL DEVICE, METHOD, AND PROGRAM

(71) Applicant: FUJIFILM Corporation, Tokyo (JP)

(72) Inventor: Takayuki Tsujimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 9 days.

(21) Appl. No.: 15/244,549

(22) Filed: Aug. 23, 2016

(65) Prior Publication Data

US 2016/0364599 A1   Dec. 15, 2016

Related U.S. Application Data

(63) Continuation of application No. PCT/JP2015/051822, filed on Jan. 23, 2015.

(30) Foreign Application Priority Data

Mar. 17, 2014 (JP) .................. 2014-052934

(51) Int. Cl.
   *G06K 9/00* (2006.01)
   *G02B 21/36* (2006.01)
   (Continued)

(52) U.S. Cl.
   CPC ........... *G06K 9/0014* (2013.01); *C12M 41/36* (2013.01); *G02B 21/14* (2013.01); *G02B 21/365* (2013.01);
   (Continued)

(58) Field of Classification Search
   CPC .......... G02B 21/00; C12M 41/00; G06K 9/00
   (Continued)

(56) References Cited

U.S. PATENT DOCUMENTS 7,467,119 B2 * 12/2008 Saidi ...................... G16H 50/20
                                                                706/21
7,711,174 B2 *  5/2010 Sammak ............ G06K 9/00127
                                                                382/133
(Continued)

FOREIGN PATENT DOCUMENTS

EP       1881061 A1    1/2008
EP       2441827 A1    4/2012
(Continued)

OTHER PUBLICATIONS

Japanese Notification of Reasons for Refusal for corresponding Japanese Application No. 2014-052934, dated Jan. 17, 2017, with a Machine translation.
(Continued)

*Primary Examiner* — Abolfazl Tabatabai
(74) *Attorney, Agent, or Firm* — Birch, Stewart, Kolasch & Birch, LLP (57) ABSTRACT

There are included a colony evaluation unit 31 that acquires an evaluation result of the cell colony in a cell image obtained by imaging the cell colony, a divided region setting unit 32 that sets a plurality of divided regions by dividing the region of the cell colony according to the evaluation result, a display control unit 34 that displays each of the plurality of divided regions, and a region deformation unit 33 that deforms the divided regions according to a change in the form of the cell colony due to an operation on the cell colony. The display control unit 34 changes a display of the divided regions before the change in form of the cell colony to a display of the divided regions after the deformation.

20 Claims, 7 Drawing Sheets

(51) Int. Cl.
*G02B 21/14* (2006.01)
*C12M 1/34* (2006.01)
*G06T 11/60* (2006.01)
*G06T 7/33* (2017.01)
*C12N 5/00* (2006.01)

(52) U.S. Cl.
CPC .......... *G06K 9/00134* (2013.01); *G06T 7/337* (2017.01); *G06T 11/60* (2013.01); *G06T 2207/10056* (2013.01); *G06T 2207/10064* (2013.01); *G06T 2207/30024* (2013.01)

(58) Field of Classification Search
USPC .......................... 382/128–134; 435/325, 375
See application file for complete search history.

(56) References Cited

U.S. PATENT DOCUMENTS

| | | | | |
|---|---|---|---|---|
| 7,920,736 | B2* | 4/2011 | Sammak | G06K 9/00127 382/133 |
| 8,986,988 | B2* | 3/2015 | Karnik | C12N 5/0068 435/283.1 |
| 2008/0241250 | A1* | 10/2008 | Emans | A61L 27/20 424/488 |
| 2013/0130228 | A1 | 5/2013 | Watakabe et al. | |
| 2014/0064594 | A1 | 3/2014 | Sugiyama et al. | |
| 2016/0177254 | A1 | 6/2016 | Kiyota | |

FOREIGN PATENT DOCUMENTS

| | | |
|---|---|---|
| JP | 2011-196867 A | 10/2011 |
| JP | 2011-229409 A | 11/2011 |
| JP | 2012-231709 A | 11/2012 |
| JP | 2013-201909 A | 10/2013 |
| WO | WO 2011/004854 A1 | 1/2011 |
| WO | WO 2011/161962 A1 | 12/2011 |

OTHER PUBLICATIONS

Extended European Search Report, dated Feb. 17, 2017, for corresponding European Application No. 15765816.2.
International Search Report issued in PCT/JP2015/051822, dated Apr. 28, 2015.
Written Opinion of the International Searching Authority issued in PCT/JP2015/051822 (PCT/ISA/237), dated Apr. 28, 2015.
English Translation of International Preliminary Report on Patentability for PCT/JP2015/051822 (including PCT/IB/373 AND PCT/ISA/237)), dated Sep. 20, 2016.
English Translation of International Search Report (PCT/ISA/210) for PCT/JP2015/051822, dated Apr. 28, 2015.
English Translation of Written Opinion of the International Searching Authority for PCT/JP2015/051822 (PCT/ISA/237), dated Apr. 28, 2015.

* cited by examiner

CELL REGION DISPLAY CONTROL DEVICE, METHOD, AND PROGRAM

CROSS-REFERENCE TO RELATED APPLICATIONS

This application is a Continuation of PCT International Application No. PCT/JP2015/051822 filed on Jan. 23, 2015, which claims priority under 35 U.S.C § 119(a) to Patent Application No. 2014-052934 filed in Japan on Mar. 17, 2014, all of which are hereby expressly incorporated by reference into the present application.

BACKGROUND OF THE INVENTION

1. Field of the Invention

The present invention relates to a cell region display control device, method, and non-transitory computer readable medium storing a program for displaying a result of the evaluation of a cell colony using a cell image obtained by imaging the cell colony.

2. Description of the Related Art

Conventionally, a method of imaging pluripotent stem cells such as ES cells, iPS cells, and STAP cells, differentiation-induced cells, or the like using a microscope and evaluating the culture state of cells by ascertaining the features of the image has been proposed.

For example, WO2011/161962A has proposed a method of acquiring the degree of circularity of a cell colony in a cell image and evaluating the cell colony based on the degree of circularity. In addition, JP2013-201909A has proposed a method of extracting a colony region from a cell image and evaluating the state of the colony region.

Here, in the cell culturing process described above, for example, for the purpose of passage, a picking operation of picking up a cell colony or a part of the cell colony by cutting out the cell colony or the part of the cell colony may be performed.

When performing such a picking operation, it is necessary to accurately specify cells to be picked up. However, since a cell itself is transparent, it may be difficult to specify a target cell just by observing a cell image captured by, for example, a bright field microscope or a phase contrast microscope.

Therefore, for example, JP2011-196867A has proposed a method of specifying a target cell in a bright field image using a fluorescent image by capturing a bright field image of a cell colony using a bright field microscope and capturing a fluorescent image of the cell colony using another microscope and by displaying the fluorescent image so as to be superimposed on the bright field image.

WO2011/004854A has proposed a method of specifying a target cell by providing a display unit below the installation place of a culture vessel and displaying the information of the target cell on the display unit.

SUMMARY OF THE INVENTION

In the method disclosed in JP2011-196867A, at a point in time when a fluorescent image is captured, it is possible to specify a target cell by observing the fluorescent image. Thereafter, however, for example, in a case where an operation such as picking is performed, cells are moved or a cell colony is deformed due to the operation. Accordingly, since a shift occurs between the actual position of the target cell and the position of the target cell on the fluorescent image, it may not be possible to perform a correct operation. In addition, in the method disclosed in JP2011-196867A, two microscopes are required. Accordingly, there is also a problem of cost increase.

Also in the method disclosed in WO2011/004854A, neither the movement of a target cell nor the deformation of a cell colony after the picking described above is taken into consideration. Therefore, as in the method disclosed in JP2011-196867A, a shift may occur between the actual position of the target cell and information displayed on a display unit.

In the case of acquiring cell images in time series, such as acquiring a motion picture, evaluating a cell colony for the cell image of each frame and sequentially updating and displaying the evaluation results in real time so that the target cell is specified may also be considered. In this case, since the movement of cells or the deformation of a cell colony due to picking affects the evaluation of the cell colony, a correct evaluation result may not be able to be obtained. In addition, evaluating the cell colony for the cell image of each frame as described above requires a processing time. Accordingly, it may not be possible to display the current state of the cell colony immediately.

In view of the aforementioned problems, it is an object of the present invention to provide a cell region display control device, method, and non-transitory computer readable medium storing a program capable of displaying the evaluation result of cell colonies accurately and quickly even in a case where cells are moved or cell colonies are deformed due to an operation performed on the cell colonies, such as picking.

A cell region display control device of the present invention comprises: an evaluation result acquisition unit that acquires an evaluation result of a cell colony in a cell image obtained by imaging the cell colony; a divided region setting unit that sets a plurality of divided regions by dividing a region of the cell colony according to the evaluation result; a display control unit that displays each of the plurality of divided regions; and a region deformation unit that deforms the divided regions according to a change in a form of the cell colony due to an operation on the cell colony. The display control unit changes a display of the divided regions before the change in form of the cell colony to a display of the divided regions after the deformation.

In the cell region display control device of the present invention described above, an operation information receiving unit that receives operation information on the cell colony can be provided, and the region deformation unit can deform the divided regions according to the operation information.

The operation information receiving unit can receive the operation information when an operation on the cell colony is manually performed.

The operation information receiving unit can receive the operation information when an operation on the cell colony is automatically performed.

The display control unit can display the divided regions so as to be superimposed on the cell image.

In addition, an image acquisition unit can acquire a cell image obtained by imaging stem cells.

The evaluation result acquisition unit can acquire an evaluation result of a degree of non-differentiation or a degree of differentiation of the cell colony.

The image acquisition unit can acquire a cell image obtained by imaging cells after differentiation induction.

The cells after differentiation induction can be myocardial cells or nerve cells.

The evaluation result acquisition unit can acquire an evaluation result of a degree of differentiation of the cell colony.

The region deformation unit can deform the divided regions based on identification information of each of the divided regions given for individual cells in the plurality of divided regions set by the divided region setting unit.

A cell region display control method of the present invention comprises: acquiring an evaluation result of a cell colony in a cell image obtained by imaging the cell colony; setting a plurality of divided regions by dividing a region of the cell colony according to the evaluation result; and displaying each of the plurality of divided regions. The divided regions are deformed according to a change in a form of the cell colony due to an operation on the cell colony, and a display of the divided regions before the change in form of the cell colony is changed to a display of the divided regions after the deformation.

A non-transitory computer readable medium storing a cell region display control program of the present invention is a divided region display control program causing a computer to function as: an evaluation result acquisition unit that acquires an evaluation result of a cell colony in a cell image obtained by imaging the cell colony; a divided region setting unit that sets a plurality of divided regions by dividing a region of the cell colony according to the evaluation result; a display control unit that displays each of the plurality of divided regions; and a region deformation unit that deforms the divided regions according to a change in a form of the cell colony due to an operation on the cell colony. The display control unit changes a display of the divided regions before the change in form of the cell colony to a display of the divided regions after the deformation.

According to the cell region display control device, method, and non-transitory computer readable medium storing a program of the invention, in the case of dividing the region of the cell colony according to the evaluation result of the cell colony and displaying each of the plurality of divided regions, in a case where the form of the cell colony has been changed by an operation on the cell colony, the divided regions are deformed according to the change in form and the display of the divided regions before the change in form of the cell colony is changed to the display of the divided regions after the deformation. Therefore, even in a case where cells are moved or cell colonies are deformed due to an operation performed on the cell colonies, such as picking, it is possible to display the evaluation result of cell colonies accurately and quickly.

DESCRIPTION OF THE PREFERRED EMBODIMENTS

Figure 1:
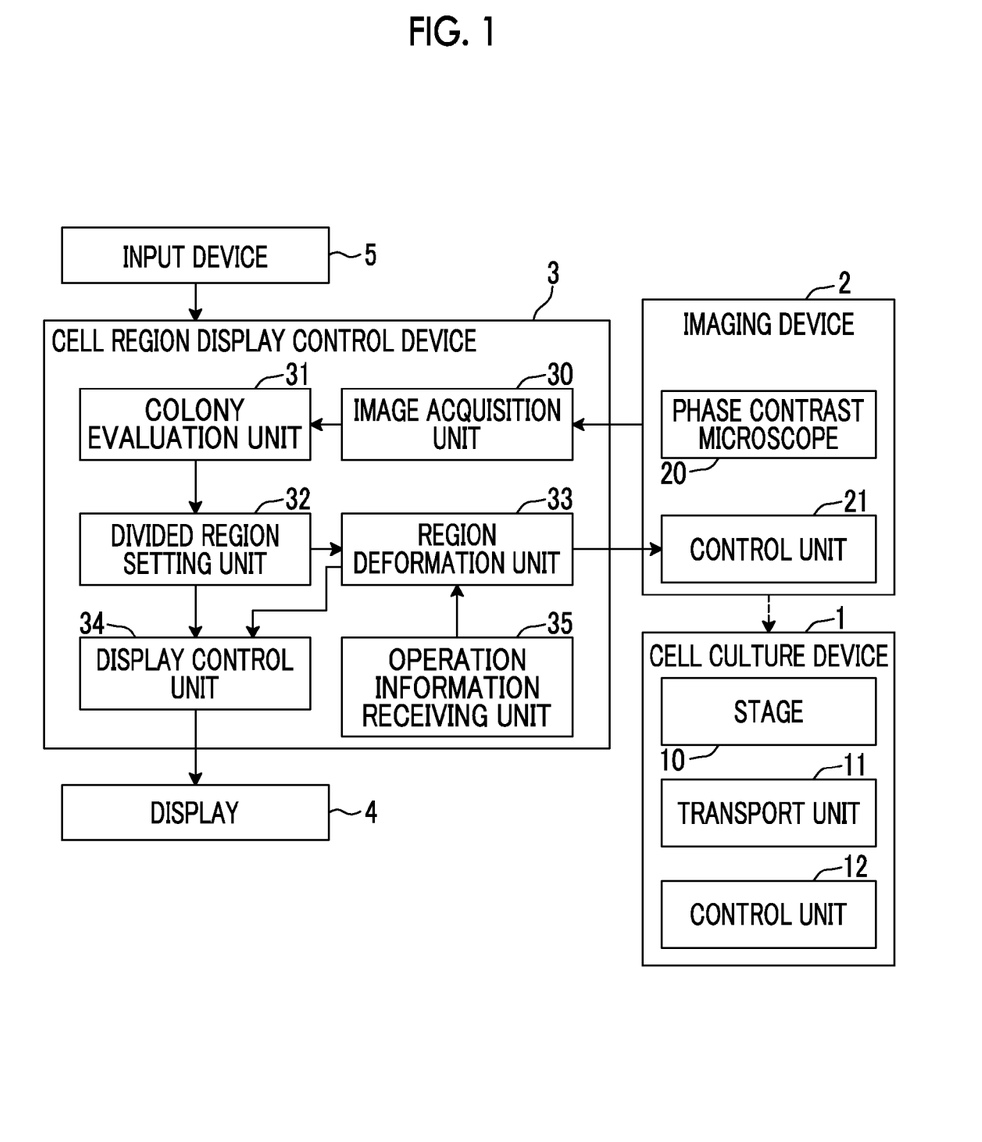
FIG. 1 is a block diagram showing the schematic configuration of a cell culture observation system using an embodiment of a cell region display control device of the present invention.

Hereinafter, a cell culture observation system using an embodiment of a cell region display control device, method, and non-transitory computer readable medium storing a program of the present invention will be described in detail with reference to the diagrams. FIG. 1 is a block diagram showing the schematic configuration of the cell culture observation system.

As shown in FIG. 1, the cell culture observation system includes a cell culture device 1, an imaging device 2, a cell region display control device 3, a display 4, and an input device 5.

The cell culture device 1 is a device for culturing cells. As cells to be cultured, for example, there are pluripotent stem cells such as iPS cells, ES cells, and STAP cells, myocardial cells or nerve cells differentiation-induced from stem cells, and cancer cells. In the cell culture device 1, a plurality of culture vessels are housed in which stem cells to be cultured are seeded on a culture medium. The cell culture device 1 includes a stage 10, a transport unit 11, and a control unit 12.

On the stage 10, a culture vessel to be imaged by the imaging device 2 is placed. The stage 10 is configured to be movable in X and Y directions perpendicular to each other within the mounting surface of the culture vessel by a driving mechanism (not shown).

The transport unit 11 selects a culture vessel to be imaged from a plurality of culture vessels housed in a predetermined position in the cell culture device 1, and transports the selected culture vessel to the stage 10. The control unit 12 controls the entire cell culture device 1, and controls not only the operation of the stage 10 or the transport unit 11 but also environmental conditions, such as the temperature, humidity, and $CO_2$ concentration in the cell culture device 1. As the configuration for adjusting the temperature, humidity, and $CO_2$ concentration, it is possible to use a known configuration.

The imaging device 2 captures an image of the cell colony in the culture vessel placed on the stage 10 in time series. The imaging device 2 includes a phase contrast microscope 20 that images cell colonies and outputs a cell image and a control unit 21 that controls the phase contrast microscope 20.

The phase contrast microscope 20 includes an imaging element, such as a complementary metal-oxide semiconductor (CMOS) sensor or a charge-coupled device (CCD) sensor, and a cell image obtained by imaging cells is output from the imaging element. Although the phase contrast microscope is used in the present embodiment, for example, a bright field microscope or a differential interference microscope may also be used without being limited to the phase contrast microscope.

The control unit 21 controls the entire imaging device 2. Specifically, the control unit 21 controls the optical magnification of the phase contrast microscope 20, the exposure time or the resolution of the imaging element, the amount of exposure of an illumination light source, and the like.

The cell region display control device 3 is formed by installing an embodiment of a cell region display control program of the present invention in a computer.

The cell region display control device 3 includes a central processing unit, a semiconductor memory, a hard disk, and the like, and an embodiment of the cell region display control program is installed in the hard disk. When the program is executed by the central processing unit, an image acquisition unit 30, a colony evaluation unit 31 (corresponding to an evaluation result acquisition unit), a divided region setting unit 32, a region deformation unit 33, a display control unit 34, and an operation information receiving unit 35 shown in FIG. 1 operate.

The image acquisition unit 30 acquires and stores a cell image of the cell colonies obtained by imaging of the imaging device 2. In the present embodiment, a cell image is acquired by performing imaging with the optical magnification of the phase contrast microscope 20 as 4× to 20×. However, the optical magnification may be changed according to a cell colony evaluation method to be described later. In the present embodiment, the image acquisition unit 30 acquires cell images captured in time series. However, the image acquisition unit 30 may acquire only a cell image of one frame at a predetermined time without being limited thereto.

The cell image may be one image obtained by imaging one cell colony, or may be a group of a plurality of images obtained by dividing one cell colony into a plurality of rectangular regions. In addition, a plurality of cell colonies may be included in one image.

The image acquisition unit 30 stores identification information for identifying the cell colony and a cell image so as to match each other. For example, in a case where one cell colony is captured as one cell image, identification information of the cell colony and the cell image are stored so as to match each other in a one-to-one manner. In a case where one cell colony is captured as cell images of a plurality of regions, identification information of the cell colony and a group of the cell images of the plurality of regions are stored so as to match each other. In addition, in a case where a plurality of cell colonies are captured as one cell image, identification information of each of the cell colonies and one cell image are stored so as to match each other.

By managing the identification information of each cell colony and a cell image so as to match each other as described above, for example, when a user inputs the identification information of the cell colony through the input device 5, it is possible to immediately read and display the cell image matched with the identification information.

The colony evaluation unit 31 acquires the cell image read from the image acquisition unit 30, specifies a region of the cell colony in the cell image, and evaluates the state of the specified cell colony. Specifically, the colony evaluation unit 31 of the present embodiment evaluates the degree of non-differentiation or the degree of differentiation of stem cell colonies.

As a method of specifying a cell colony region, for example, it is desirable to specify a cell colony region by converting a cell image into a binary image and then automatically extracting a cell colony region by template matching or the like. For the automatic extraction of a cell colony region, other known methods may be used without being limited to the method described above.

In addition, without being limited to the automatic extraction, a cell image may be displayed on the display 4 by the display control unit 34, the user may designate a cell colony region in the cell image using the input device 5, and the colony evaluation unit 31 may acquire position information, such as the designated coordinates.

As a method of evaluating the degree of differentiation or the degree of non-differentiation of stem cells in the stem cell colony, for example, it is preferable to acquire the distribution state of individual cells in the stem cell colony and evaluate whether the stem cells are in a differentiated state or in an undifferentiated state based on the distribution state. Specifically, the density of stem cells may be calculated, and stem cells in a range where the density is higher than a predetermined threshold value may be evaluated to be in an undifferentiated state and stem cells in a range where the density is lower than the threshold value may be evaluated to be in a differentiated state.

For example, the distribution state of individual cells may be acquired by detecting the pattern of the nucleoli of cells, or may be acquired by detecting the pattern of a halo caused by diffracted light passing through the cells. When illumination light passes through the cells, diffraction occurs. Then, in a case where the distance between cells (slit gap) is an integral multiple of the wavelength of illumination light, the phase of diffracted light (±first-order diffracted light) and the phase of direct light (zero-order diffracted light) match each other, and high-brightness artifacts occur. The high-brightness artifacts are a halo.

In addition, the differentiated state or the undifferentiated state may be evaluated based on the shape of individual cells without being limited to the density of stem cells. For example, the degree of circularity of individual cells may be calculated using pattern matching or the like, and stem cells having a degree of circularity greater than a predetermined threshold value may be evaluated to be in an undifferentiated state and stem cells having a degree of circularity less than the threshold value may be evaluated to be in a differentiated state.

The differentiated state or the undifferentiated state may also be evaluated based on the brightness distribution of the cell image of the stem cell colony region. Specifically, the brightness distribution of the cell image of the stem cell colony region may be calculated, and stem cells in a range where the brightness is higher than a predetermined threshold value may be evaluated to be in an undifferentiated state and stem cells in a range where the brightness is lower than the threshold value may be evaluated to be in a differentiated state.

In addition, the differentiated state or the undifferentiated state may be evaluated based on the distribution state of the halo. Specifically, a halo may be extracted from the cell image of the stem cell colony region, and stem cells in a range where the halo is less than a predetermined threshold value may be evaluated to be in an undifferentiated state and stem cells in a range where the halo is greater than the threshold value may be determined to be in a differentiated state.

In a case where a plurality of stem cell colonies are present in a cell image, the degree of circularity of each stem cell colony may be evaluated, and it may be evaluated that differentiation has occurred for a stem cell colony having a degree of circularity equal to or less than a predetermined threshold value. In this manner, the degree of differentiation or the degree of non-differentiation of stem cells in the stem cell colony may be evaluated as described above.

For the degree of non-differentiation or the degree of differentiation of stem cells, it is possible to use other known evaluation methods without being limited to the evaluation method described above.

Figure 2:
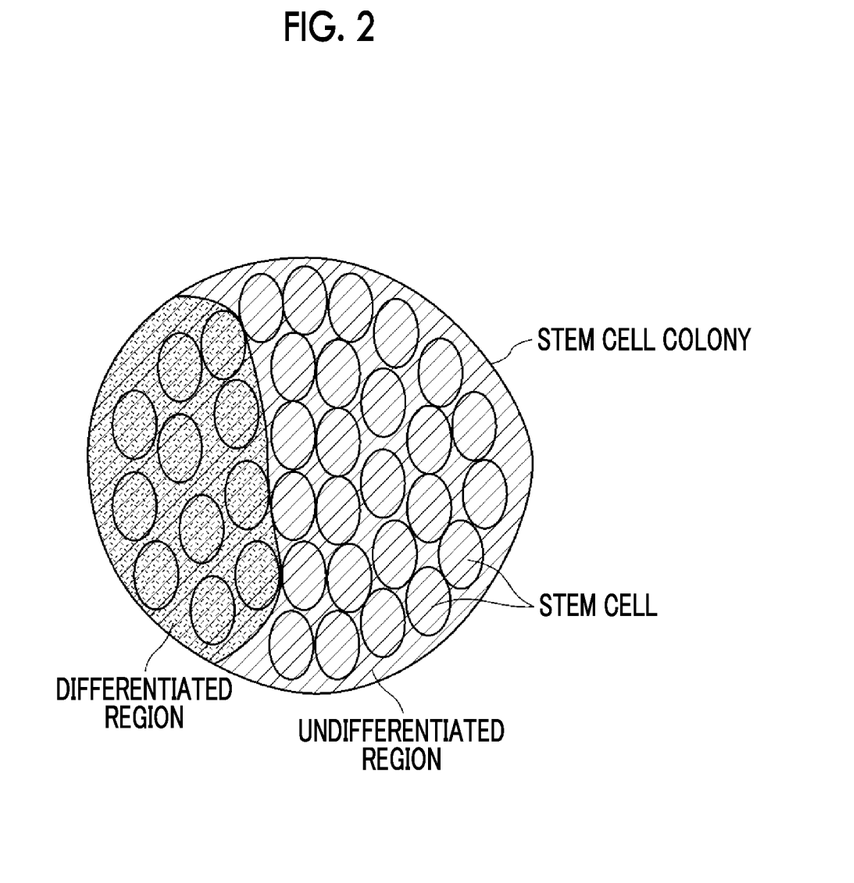
FIG. 2 is a diagram showing an example of a differentiated region and an undifferentiated region.

The divided region setting unit 32 sets a plurality of divided regions by dividing the region of the cell colony based on the evaluation result of the colony evaluation unit 31. The divided region setting unit 32 in the present embodiment sets an undifferentiated region and a differentiated region by dividing the cell colony region based on the evaluation result of the degree of differentiation or the degree of non-differentiation in the colony evaluation unit 31. FIG. 2 shows an example of the differentiated region and the undifferentiated region set by the divided region setting unit 32.

For the method of setting a differentiated region and an undifferentiated region, as shown in FIG. 2, a differentiated region including stem cells in a differentiated state and an undifferentiated region including undifferentiated cells may be set as a closed region expressed by a smooth curve, such as a free curve. Alternatively, a differentiated region including stem cells in a differentiated state and an undifferentiated region including undifferentiated cells may be set as a rough region having a shape set in advance, such as a circular region, an elliptical region, or a rectangular region. In addition, the differentiated region and the undifferentiated region do not necessarily need to be set as one region. For example, each region of individual cells in a differentiated state may be set as a differentiated region, and each region of individual cells in an undifferentiated state may be set as an undifferentiated region.

In addition, for each stem cell in the stem cell colony, the divided region setting unit 32 gives identification information based on the degree of differentiation or the degree of non-differentiation. Specifically, for example, identification information of the numerical value "1" is given for stem cells in the undifferentiated state, and identification information of the numerical value "2" is given for stem cells in the differentiated state. The type of identification information is not limited to the numerical values described above, and other indicators, such as characters, may be given.

In the present embodiment, for all stem cells in the stem cell colony, the identification information is given based on the degree of differentiation or the degree of non-differentiation of individual stem cells. However, without being limited thereto, for example, only for stem cells present in the vicinity of the boundary between the undifferentiated region and the differentiated region, the identification information may be given based on a region where the stem cells belong. In addition, only for stem cells present in the vicinity of the contour of the undifferentiated region and the differentiated region, the identification information may be given. The vicinity of the boundary or the contour described above may be set to a range within a distance set in advance from the boundary or the contour. For example, the vicinity of the boundary or the contour described above may be set to about 10 μm to 50 μm.

The display control unit 34 acquires the cell image read from the image acquisition unit 30 and acquires the information of the plurality of divided regions set by the divided region setting unit 32, and displays the cell image and an image showing the divided regions on the display 4 so as to be superimposed on each other. As the image showing the divided regions, a translucent image that can be observed after passing through the cell image may be used, or an image showing the contour of the divided region may be used. The respective divided regions may be displayed in different colors. For example, one divided region may be displayed in red, and the other divided region may be displayed in blue.

When a predetermined operation is performed on a stem cell colony to change the state of the stem cell colony, the region deformation unit 33 deforms each divided region set by the divided region setting unit 32 according to the state change. Specifically, the region deformation unit 33 of the present embodiment deforms the differentiated region and the undifferentiated region described above according to a change in the state of the stem cell colony.

As the predetermined operation on the stem cell colony, for example, there is an operation of picking undifferentiated cells in the stem cell colony, an operation of sucking out cells or other objects from the stem cell colony, or an injection operation on the stem cell colony using a syringe. However, any operation is possible as long as the state of the stem cell colony is changed by the operation.

Figure 3:
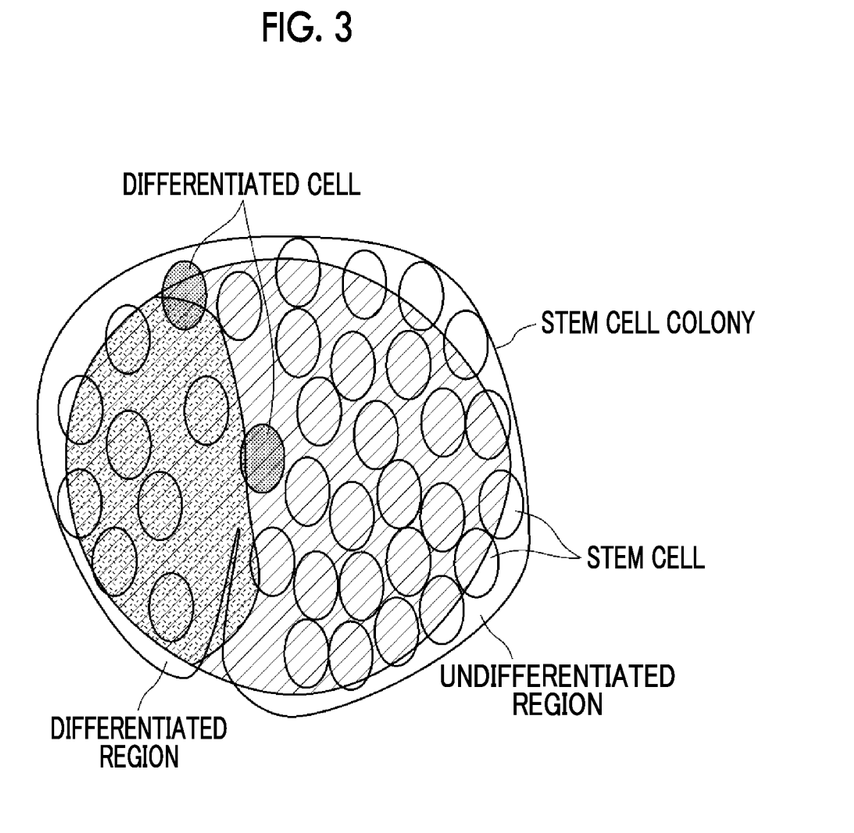
FIG. 3 is a diagram illustrating the relationship between the form of a stem cell colony after cutting and a differentiated region and an undifferentiated region before cutting.

For the stem cell colony shown in FIG. 2, in the case of picking undifferentiated cells for passage, the stem cell colony is deformed into the form shown in FIG. 3 due to the cutting operation. Accordingly, the arrangement of undifferentiated cells and differentiated cells is changed. In such a case, in the case of performing display while maintaining the differentiated region and the undifferentiated region set by the divided region setting unit 32, differentiated cells that have been present in the differentiated region before the cutting operation are moved to the outside of the differentiated region due to the cutting operation, thereby being present in the undifferentiated region, as shown in FIG. 3. The moved differentiated cells affect the subsequent cutting of undifferentiated cells.

Figure 4:
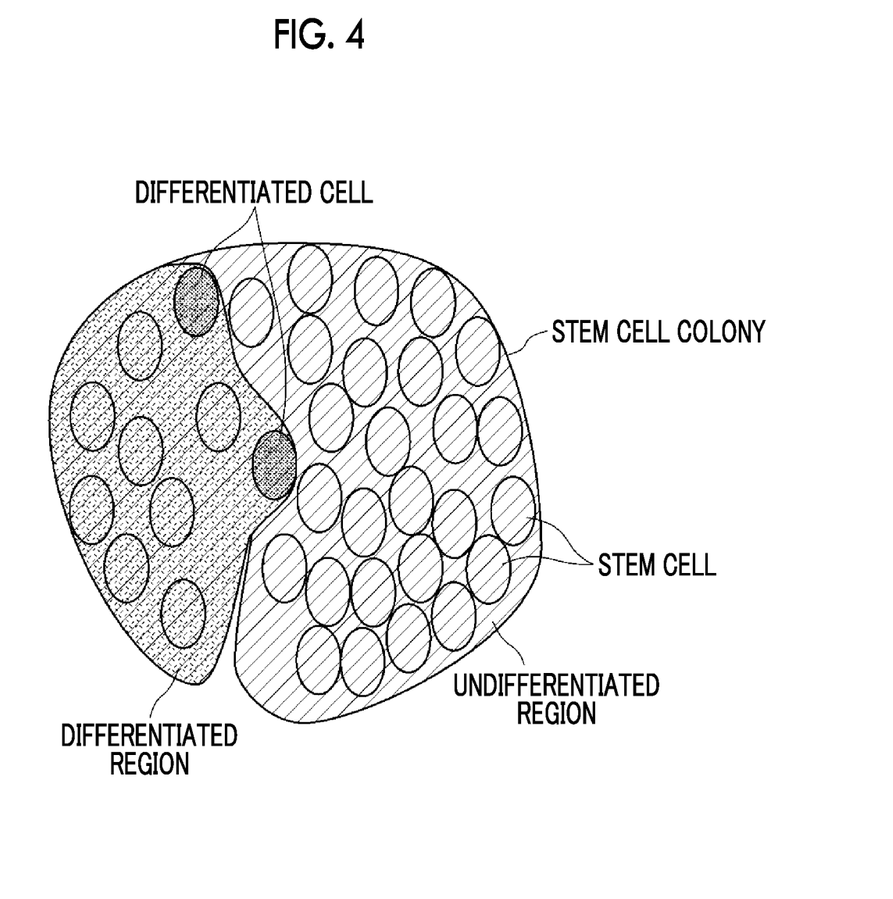
FIG. 4 is a diagram showing an example of deforming a differentiated region and an undifferentiated region according to a change in the form of the stem cell colony.

Therefore, the region deformation unit 33 of the present embodiment deforms each divided region set by the divided region setting unit 32 according to a change in the state of the stem cell colony as described above. Specifically, using the identification information given for each stem cell by the divided region setting unit 32, the region deformation unit 33 deforms the undifferentiated region and the differentiated region so that stem cells, for which "1" that is the identification information of undifferentiated cells is given, are included in the undifferentiated region and stem cells, for which "2" that is the identification information of differentiated cells is given, are included in the differentiated region. FIG. 4 shows an example of an undifferentiated region and a differentiated region after deforming the undifferentiated region and the differentiated region shown in FIG. 3.

The information of the undifferentiated region and the differentiated region deformed by the region deformation unit 33 is output to the display control unit 34, and the display control unit 34 displays an image showing the differentiated region and the undifferentiated region after the deformation that has been changed from the image showing the differentiated region and the undifferentiated region before a predetermined operation on the stem cell colony.

Thus, by changing the display of the undifferentiated region and the differentiated region according to a change in the state of the stem cell colony due to an operation on the stem cell colony, it is possible to appropriately perform the subsequent cutting of undifferentiated cells.

In addition, since the differentiated region and the undifferentiated region set by the divided region setting unit 32 are deformed instead of evaluating the stem cell colony again after performing a predetermined operation on the stem cell colony, processing for evaluating the stem cell colony is not necessary. Accordingly, it is possible to change the display at a higher speed. In addition, even if the density of stem cells is changed or the stem cell colony is deformed by a predetermined operation on the stem cell colony, the stem cell colony is not re-evaluated. Therefore, since there is no problem of incorrect evaluation due to deformation, density changes, or the like, it is possible to appropriately display the differentiated region and the undifferentiated region.

The operation information receiving unit 35 receives information indicating that the above-described predetermined operation on the stem cell colony has been performed. In the present embodiment, in a case where the operation information is received by the operation information receiving unit 35, the region deformation unit 33 performs processing for deforming the differentiated region and the undifferentiated region.

Specifically, for example, in a case where the user manually performs a predetermined operation on the stem cell colony, information indicating that the operation has been performed by the user is input using the input device 5, and the input information is received as operation information by the operation information receiving unit 35.

In the case of automatically performing a predetermined operation on the stem cell colony, for example, in the case of automatically performing picking from the stem cell colony, information indicating that the picking has been performed is received as operation information by the operation information receiving unit 35. Such a picking device is not shown in FIG. 1.

The input device 5 includes a mouse, a keyboard, and the like, and receives an operation input from the user. For example, the input device 5 can receive a setting input of the optical magnification of the phase contrast microscope 20 or the operation information described above.

Figure 5:
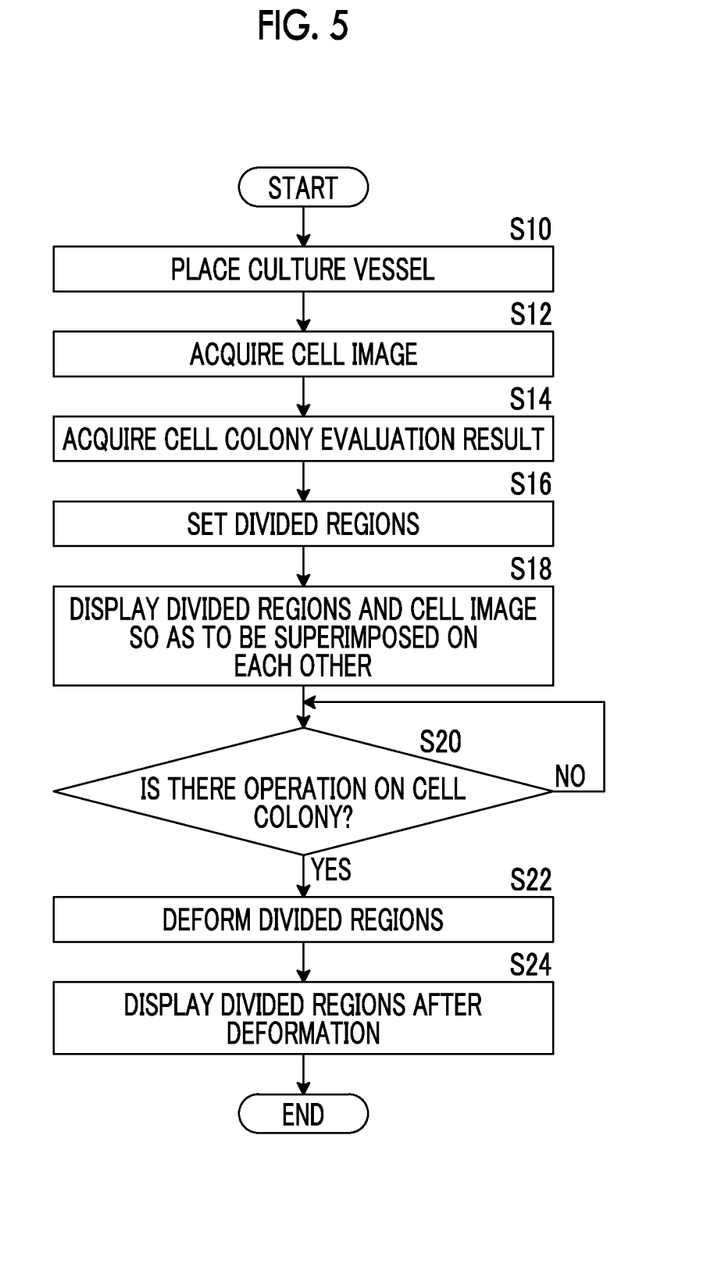
FIG. 5 is a flowchart illustrating the operation of the cell culture observation system using an embodiment of the cell region display control device of the present invention.

Next, the operation of the above-described cell culture observation system will be described with reference to the flowchart shown in FIG. 5.

First, in the cell culture device 1, the transport unit 11 selects a culture to be imaged from a plurality of culture vessels housed therein, and places the selected culture vessel on the stage 10 (S10).

Then, an image of the cell colony in the culture vessel is captured in time series by the phase contrast microscope 20 of the imaging device 2, and the cell image captured in time series is acquired by the image acquisition unit 30 of the cell region display control device 3 (S12).

Then, the cell image of a predetermined frame acquired by the image acquisition unit 30 is read by the colony evaluation unit 31, the cell colony is evaluated by the colony evaluation unit 31, and the evaluation result is acquired (S14). In the present embodiment, the degree of differentiation or the degree of non-differentiation of individual stem cells of the stem cell colony is evaluated as described above.

The evaluation result of the colony evaluation unit 31 is output to the divided region setting unit 32, and the divided region setting unit 32 divides the region of the stem cell colony into a plurality of regions based on the input evaluation result (S16). In the present embodiment, the region of the stem cell colony is set to be divided into the undifferentiated region and the differentiated region as described above.

Then, the cell image acquired by the image acquisition unit 30 and the information of the undifferentiated region and the differentiated region set by the divided region setting unit 32 are output to the display control unit 34, and the display control unit 34 displays the cell image and an image, which shows the differentiated region and the undifferentiated region, on the display 4 so that the image showing the differentiated region and the undifferentiated region is superimposed on the cell image (S18).

Then, in a case where the information of the operation on the cell colony is received by the operation information receiving unit 35 (S20, YES), information indicating the reception of the operation information is output to the region deformation unit 33, and the region deformation unit 33 deforms the undifferentiated region and the differentiated region based on the identification information given for individual stem cells as described above (S22).

The information of the differentiated region and the undifferentiated region deformed by the region deformation unit 33 is output to the display control unit 34, and the display control unit 34 displays the input differentiated region and undifferentiated region after the deformation so as to be superimposed on the cell image of the cell colony after the operation (S24).

Figure 6:
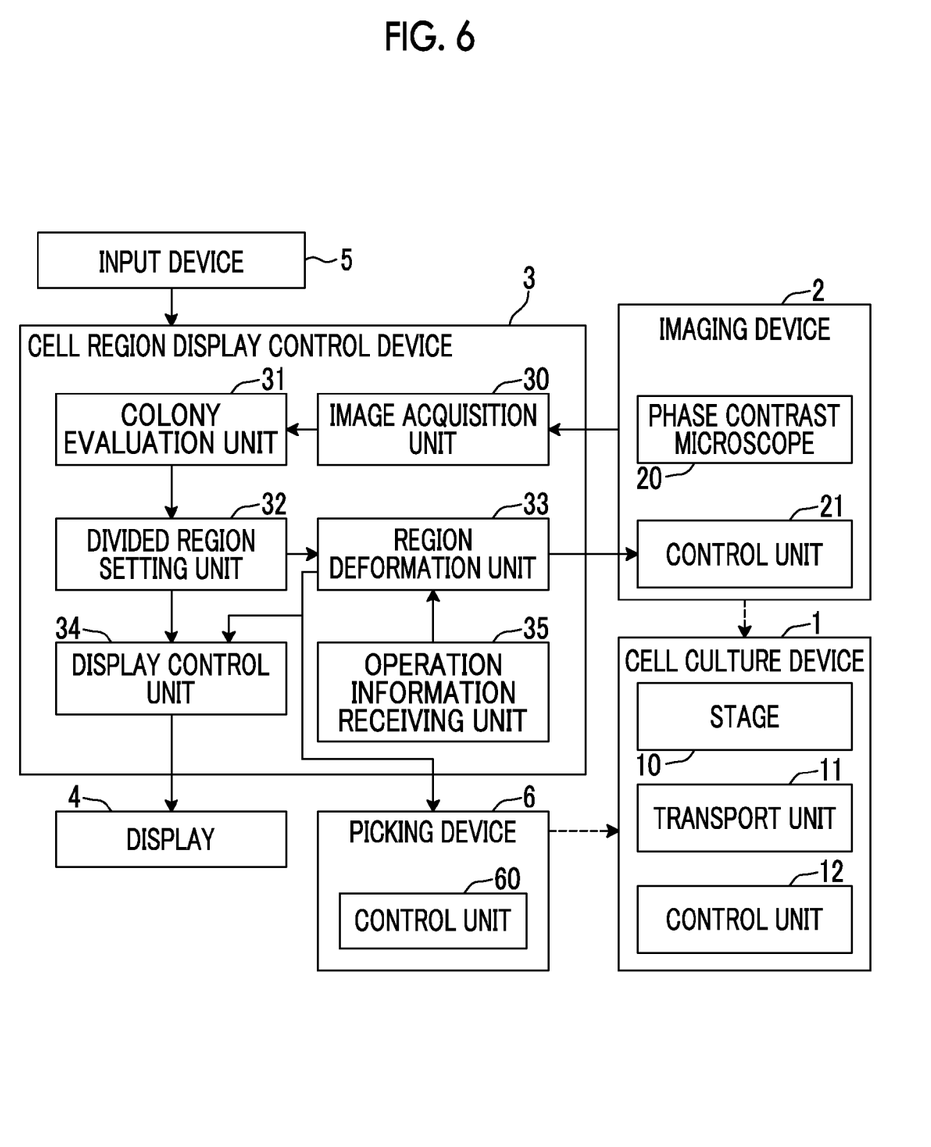
FIG. 6 is a block diagram showing the schematic configuration of a cell culture observation system using another embodiment of the cell region display control device of the present invention.

In the cell culture observation system of the embodiment described above, in the case of automatically performing an operation, such as picking, on the cell colony, the information of the differentiated region and the undifferentiated region after deformation that is acquired by the region deformation unit 33 may also be used in the next picking. Specifically, as shown in FIG. 6, in a case where a picking device 6 for automatically picking a cell colony is provided, the region deformation unit 33 outputs the information of the differentiated region and the undifferentiated region after deformation to a control unit 60, and the control unit 60 controls a picking mechanism to perform the next cutting operation using the information of the input differentiated region and undifferentiated region after the deformation. For example, in a case where the stem cell colony is cut and the undifferentiated region and the differentiated region are deformed as shown in FIG. 7, it is preferable to control the picking mechanism so that the stem cell colony is cut in a direction indicated by the arrow in FIG. 7.

Figure 7:
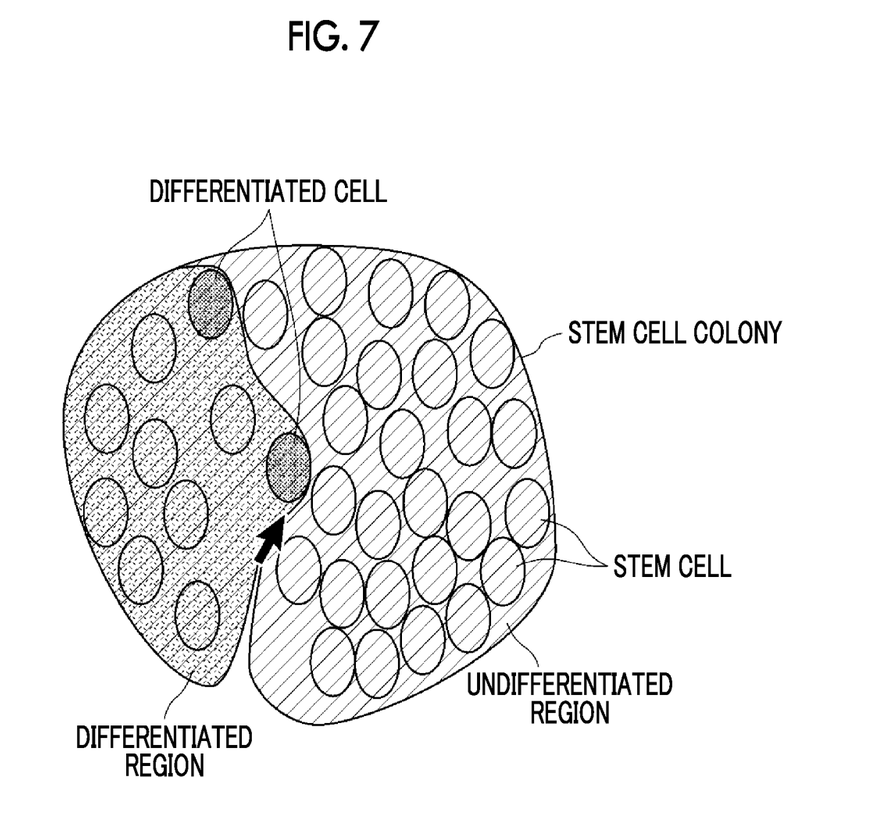
FIG. 7 is a diagram showing an example when navigation display is performed for a cell image.

In a case where the user performs picking or the like manually instead of performing the picking automatically as described above, the display control unit 34 may display the arrow shown in FIG. 7 so as to be superimposed on the cell image, so that navigation display when the user performs picking is performed. That is, based on the information of the undifferentiated region and the differentiated region after deformation, navigation display for the next operation of the user may be performed.

In the above explanation of the embodiment, a cell image is acquired by imaging the stem cell colony, and differentiation and non-differentiation are evaluated. However, without being limited thereto, a cell image may be acquired by imaging the cell colony after induction of differentiation, and the degree of differentiation may be evaluated according to whether or not individual cells in the cell colony are differentiated into desired cells.

In this case, the divided region setting unit 32 sets, as divided regions, a region where the degree of differentiation has increased to the desired extent and a region where the degree of differentiation has not increased to the desired extent, and the region deformation unit 33 deforms each divided region based on the identification information given for the cells of each region when a predetermined operation has been performed on the cell colony, as in the embodiment described above.

As cells after differentiation induction, for example, there are myocardial cells or nerve cells. The evaluation of cells after differentiation induction is not limited to the degree of differentiation described above. For example, for myocardial cells, beating may be evaluated, and a region where cells that are beating are distributed and a region where cells that do not beat are distributed may be set as divided regions. In the case of nerve cells, the density or the length of the axon of a nerve may be calculated, and a region where the density or the length of the axon is equal to or greater than a predetermined threshold value and a region where the density or the length of the axon is less than the threshold value may be set as divided regions.

In the cell culture observation system of the embodiment described above, in a case where the operation information is received by the operation information receiving unit 35, the region deformation unit 33 deforms the divided regions. However, without being limited thereto, divided regions may be deformed for each frame according to the frame rate of cell images acquired in time series in the imaging device 2, for example. At this time, divided regions may be deformed every multiple frames without being limited to each frame.

In the cell culture observation system of the embodiment described above, a cell colony is evaluated by the colony evaluation unit 31 in the cell region display control device 3, and the evaluation result is acquired. However, the cell region display control device of the present invention does not necessarily perform the evaluation of the cell colony in its own device, and the cell region display control device may acquire the evaluation result of the cell colony from other devices.

EXPLANATION OF REFERENCES

1: cell culture device
2: imaging device
3: cell region display control device
4: display
5: input device
6: picking device
10: stage
11: transport unit
12: control unit
20: phase contrast microscope
21: control unit
30: image acquisition unit
31: colony evaluation unit
32: divided region setting unit
33: region deformation unit
34: display control unit
35: operation information receiving unit
60: control unit

What is claimed is:

1. A cell region display control device, comprising:
a processing circuitry configured to
acquire an evaluation result of a cell colony in a cell image obtained by imaging the cell colony;
set a plurality of divided regions by dividing a region of the cell colony on the cell image according to the evaluation result;
display each of the plurality of divided regions; and
deform the divided regions on the cell image according to a change in a form of the cell colony due to an operation on the cell colony,
wherein the processing circuitry changes a display of the divided regions before the change in form of the cell colony to a display of the divided regions after the deformation.

2. The cell region display control device according to claim 1, the processing circuitry further configured to:
receive operation information on the cell colony,
wherein the processing circuitry deforms the divided regions according to the operation information.

3. The cell region display control device according to claim 2,
wherein the processing circuitry receives the operation information when an operation on the cell colony is manually performed.

4. The cell region display control device according to claim 3,
wherein the processing circuitry displays the divided regions so as to be superimposed on the cell image.

5. The cell region display control device according to claim 3,
wherein the processing circuitry acquires a cell image obtained by imaging stem cells.

6. The cell region display control device according to claim 2,
wherein the processing circuitry receives the operation information when an operation on the cell colony is automatically performed.

7. The cell region display control device according to claim 6,
wherein the processing circuitry displays the divided regions so as to be superimposed on the cell image.

8. The cell region display control device according to claim 6,
wherein the processing circuitry acquires a cell image obtained by imaging stem cells.

9. The cell region display control device according to claim 2,
wherein the processing circuitry displays the divided regions so as to be superimposed on the cell image.

10. The cell region display control device according to claim 2,
wherein the processing circuitry acquires a cell image obtained by imaging stem cells.

11. The cell region display control device according to claim 10,
wherein the processing circuitry acquires an evaluation result of a degree of non-differentiation or a degree of differentiation of the cell colony.

12. The cell region display control device according to claim 1,
wherein the processing circuitry displays the divided regions so as to be superimposed on the cell image.

13. The cell region display control device according to claim 1,
wherein the processing circuitry acquires a cell image obtained by imaging stem cells.

14. The cell region display control device according to claim 13,
wherein the processing circuitry acquires an evaluation result of a degree of non-differentiation or a degree of differentiation of the cell colony.

15. The cell region display control device according to claim 1,
wherein the processing circuitry acquires a cell image obtained by imaging cells after differentiation induction.

16. The cell region display control device according to claim 15,
wherein the cells after differentiation induction are myocardial cells or nerve cells.

17. The cell region display control device according to claim 15,
wherein the processing circuitry acquires an evaluation result of a degree of differentiation of the cell colony.

18. The cell region display control device according to claim 1, wherein the processing circuitry deforms the divided regions based on identification information of each of the divided regions given for individual cells in the plurality of divided regions set by the processing circuitry.

19. A cell region display control method using the cell region display control device according to claim 1, comprising:

acquiring an evaluation result of a cell colony in a cell image obtained by imaging the cell colony;

setting a plurality of divided regions by dividing a region of the cell colony according to the evaluation result; and displaying each of the plurality of divided regions, wherein the divided regions are deformed according to a change in a form of the cell colony due to an operation on the cell colony, and a display of the divided regions before the change in form of the cell colony is changed to a display of the divided regions after the deformation.

20. A non-transitory computer readable medium storing a cell region display control program, executable by processing circuitry, to cause a computer to:

acquire an evaluation result of a cell colony in a cell image obtained by imaging the cell colony;

set a plurality of divided regions by dividing a region of the cell colony on the cell image according to the evaluation result;

display each of the plurality of divided regions; and deform the divided regions on the cell image according to a change in a form of the cell colony due to an operation on the cell colony, wherein a display of the divided regions changes before the change in form of the cell colony to a display of the divided regions after the deformation.

* * * * *